(12) United States Patent
Liu et al.

(10) Patent No.: US 9,416,066 B2
(45) Date of Patent: Aug. 16, 2016

(54) CATALYST SUPPORTS MADE FROM SILICON CARBIDE COVERED WITH TIO$_2$ FOR FISCHER-TROPSCH SYNTHESIS

(71) Applicants: SICAT CATALYSTS, INC., Wilmington (DE); CENTRE NATIONAL DE LA RECHERCHE SCIENTIFIQUE, Paris (FR); UNIVERSITE DE STRASBOURG, Strasbourg (FR)

(72) Inventors: Yuefeng Liu, Strasbourg (FR); Cuong Pham-Huu, Strasbourg (FR); Patrick Nguyen, Strasbourg (FR); Charlotte Pham, Strasbourg (FR)

(73) Assignees: Sicat Catalysts, Inc., Wilmington, DE (US); Centre National de la Recherche Scientifique, Paris (FR); Universite de Strasbourg, Strasbourg (FR)

( * ) Notice: Subject to any disclaimer, the term of this patent is extended or adjusted under 35 U.S.C. 154(b) by 0 days.

(21) Appl. No.: 14/411,543

(22) PCT Filed: Jun. 24, 2013

(86) PCT No.: PCT/FR2013/051465
§ 371 (c)(1),
(2) Date: Dec. 29, 2014

(87) PCT Pub. No.: WO2014/001697
PCT Pub. Date: Jan. 3, 2014

(65) Prior Publication Data
US 2015/0191401 A1 Jul. 9, 2015

(30) Foreign Application Priority Data

Jun. 26, 2012 (FR) .................................... 12 56028
Jul. 31, 2012 (FR) .................................... 12 57446

(51) Int. Cl.
| | | |
|---|---|---|
| C07C 27/00 | (2006.01) |
| C07C 1/04 | (2006.01) |
| B01J 35/00 | (2006.01) |
| B01J 37/02 | (2006.01) |
| B01J 21/06 | (2006.01) |
| B01J 23/745 | (2006.01) |
| B01J 23/75 | (2006.01) |
| B01J 27/224 | (2006.01) |
| B01J 35/04 | (2006.01) |
| C10G 2/00 | (2006.01) |
| B01J 35/10 | (2006.01) |
| B01J 37/08 | (2006.01) |

(52) U.S. Cl.
CPC ............... *C07C 1/043* (2013.01); *B01J 21/063* (2013.01); *B01J 23/745* (2013.01); *B01J 23/75* (2013.01); *B01J 27/224* (2013.01); *B01J 35/0006* (2013.01); *B01J 35/04* (2013.01); *B01J 35/1009* (2013.01); *B01J 35/1014* (2013.01); *B01J 37/0203* (2013.01); *B01J 37/0205* (2013.01); *B01J 37/0207* (2013.01); *B01J 37/0209* (2013.01); *B01J 37/0213* (2013.01); *B01J 37/08* (2013.01); *C07C 1/0445* (2013.01); *C10G 2/332* (2013.01)

(58) Field of Classification Search
CPC .... C10G 2/332; B01J 35/0006; B01J 21/063; B01J 23/745; B01J 23/75; B01J 27/224; B01J 37/0203
USPC .......................................... 502/178; 517/715
See application file for complete search history.

(56) References Cited

U.S. PATENT DOCUMENTS

2006/0110308 A1   5/2006   Gupta

FOREIGN PATENT DOCUMENTS

| FR | 2 887 545 A1 | 12/2006 |
|---|---|---|
| WO | 2009/098393 A2 | 8/2009 |
| WO | 2010/029235 A1 | 3/2010 |
| WO | 2012/038621 A1 | 3/2012 |

OTHER PUBLICATIONS

Nguyen et al., innovative porous SiC-based materials: From nanoscopic understandings to tunable carriers serving catalytic needs (Applied Catalysis A: General 391 (2011) 443-454).*
Kouame, "Preliminary study of the use of [beta]-SiC foam as a photocatalytic support for water treatment", Catalysis Today, Jan. 1, 2010, USA.
Patrick Nguyen et al., "ChemInForrn Abstract: Innovative Porous SiC-Based Materials: From Nanoscopic Understandings to Turnable Carriers Serving Catalytic Needs", ChemInForm, May 3, 2011, vol. 42 No. 18, USA.

* cited by examiner

*Primary Examiner* — Jafar Parsa
(74) *Attorney, Agent, or Firm* — Jordan IP Law, LLC; Todd A. Vaughn

(57) ABSTRACT

Catalysts supports and catalysts capable of being used in heterogeneous catalysis. The catalyst support belongs to the porous supports based on silicon carbide (SiC), in particular, based on β-SiC, modified by a surface deposit of TiO$_2$.

9 Claims, 10 Drawing Sheets

Figure 1:
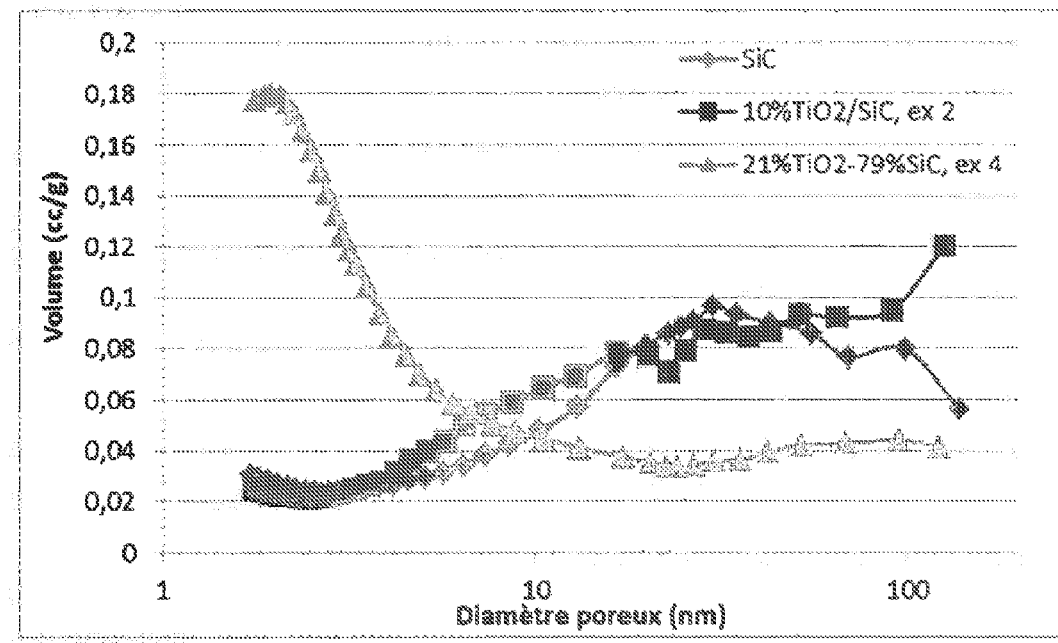
Figure 1:
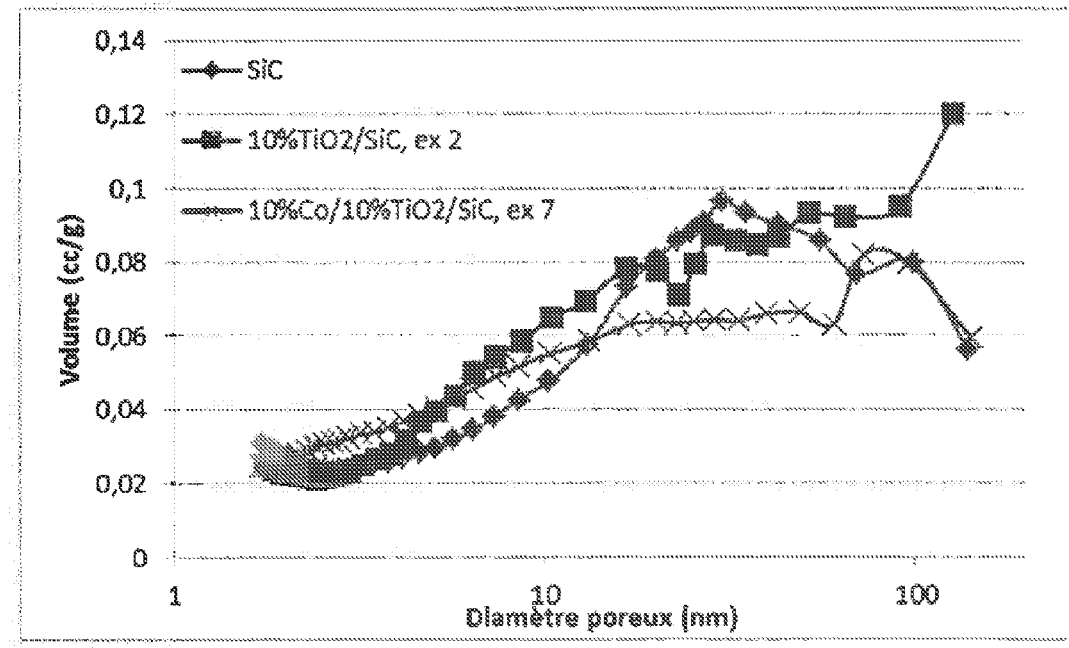

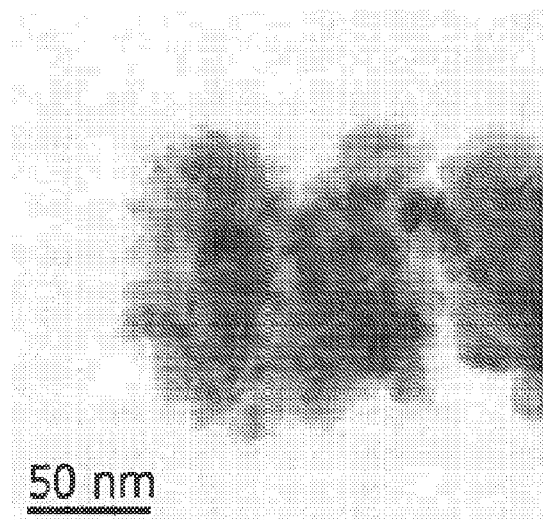 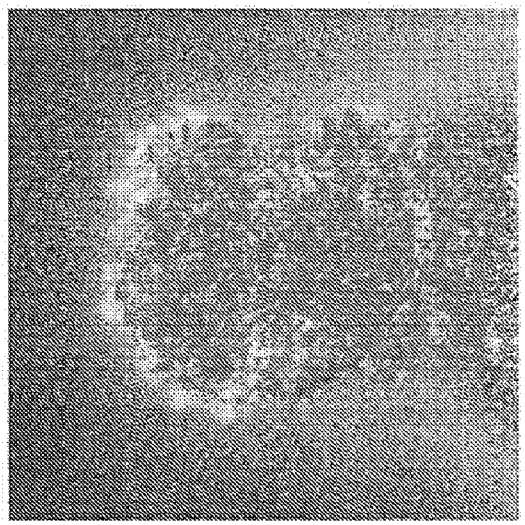
Figure 4 (a)  Figure 4 (b)
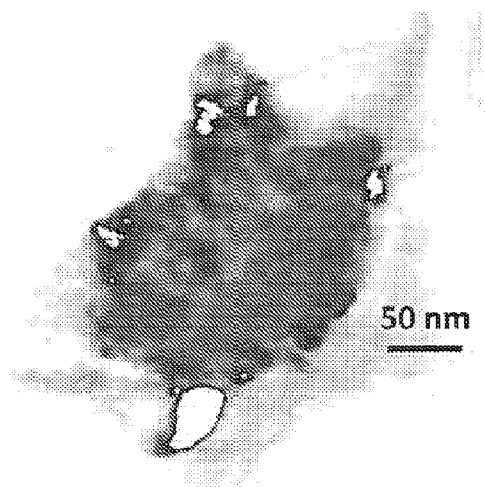 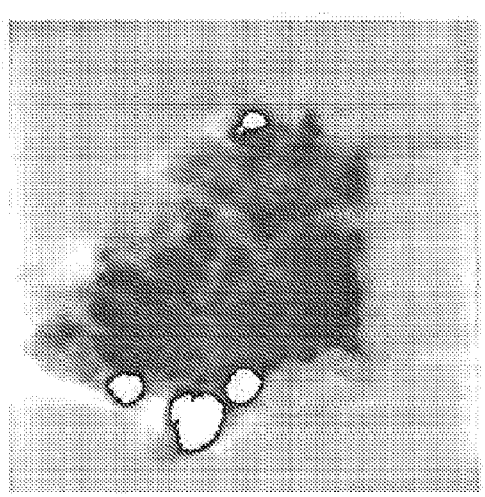
Figure 6 (a)  Figure 6 (b)

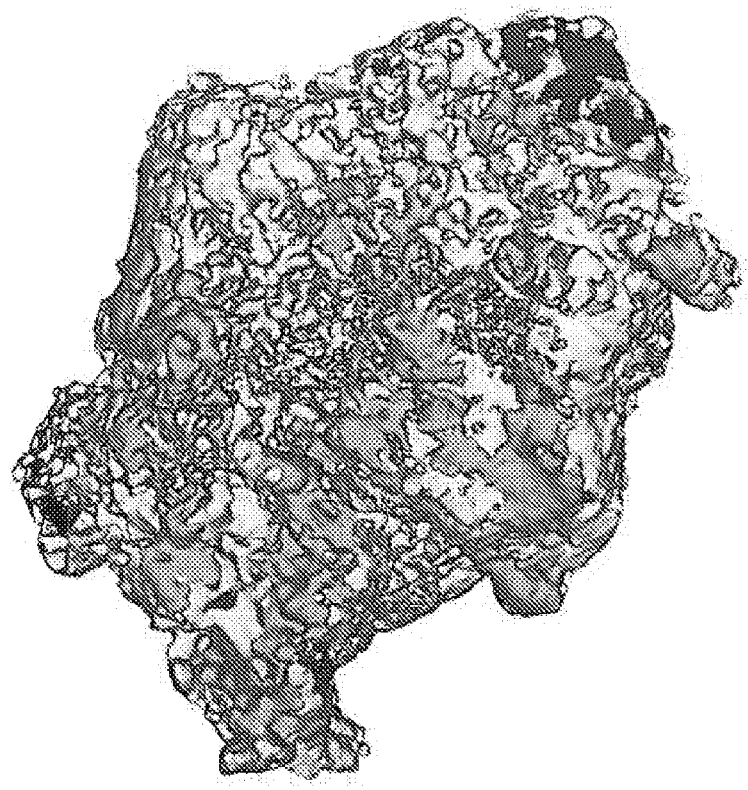
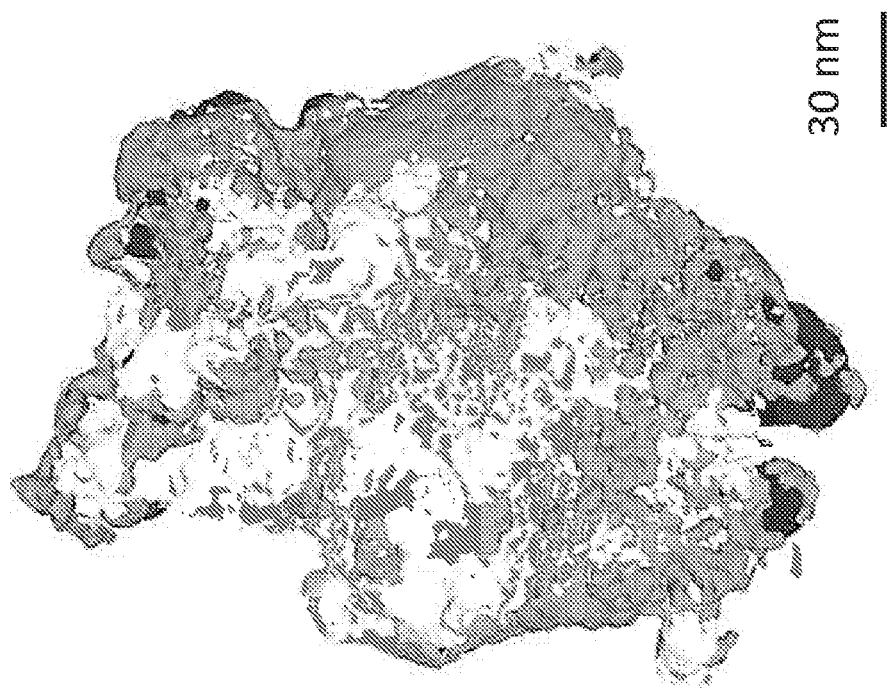
Figure 5

Figure 7
← Figure 7(a)
↓ Figures 7 (b), (c), (d)
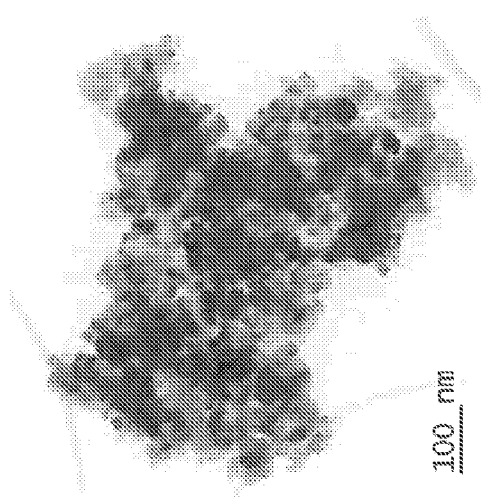
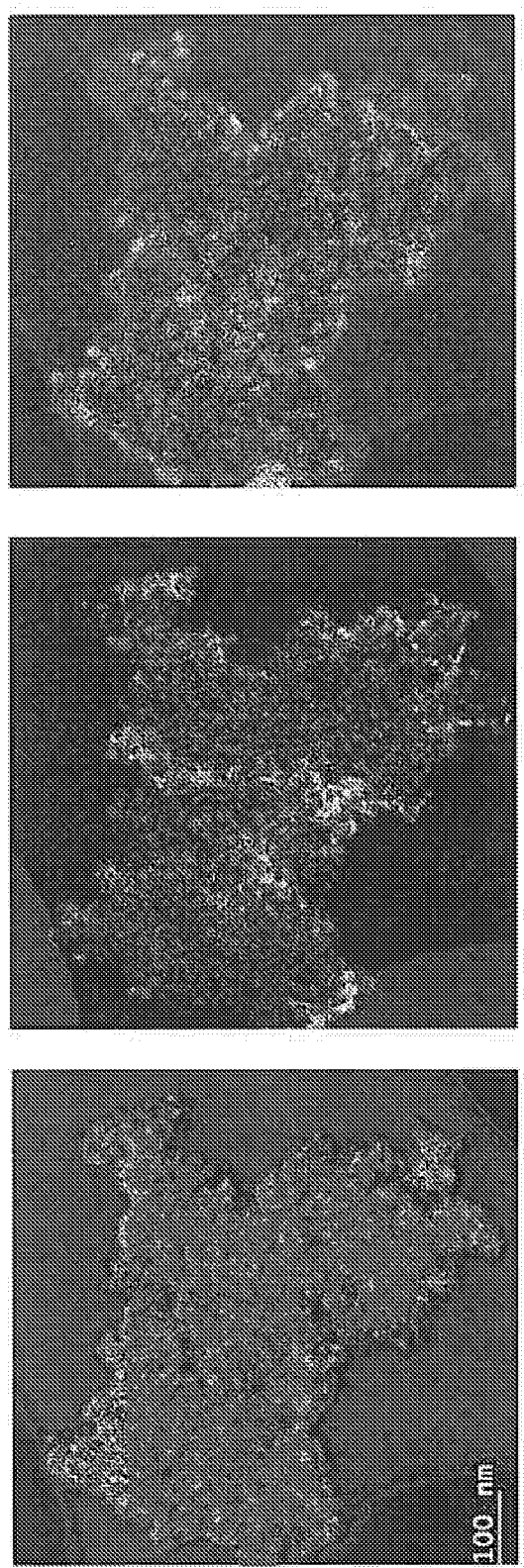

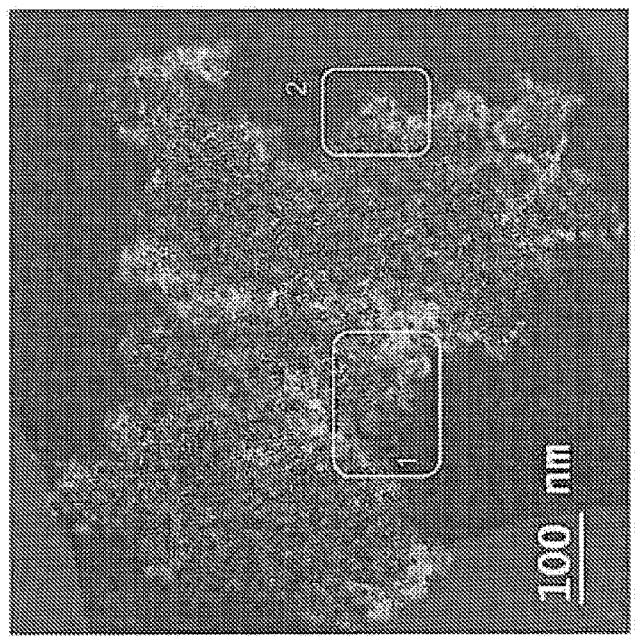
Figure 7 (e),(f)
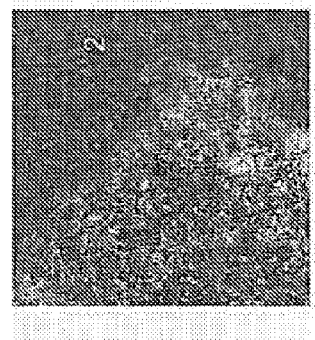
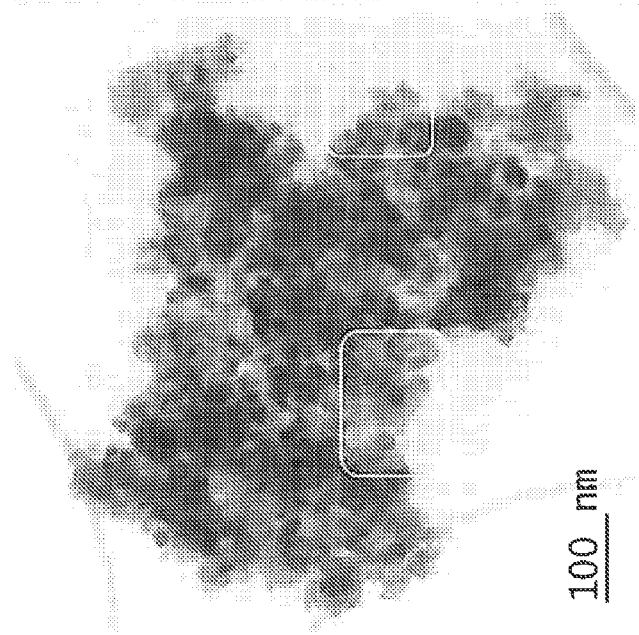
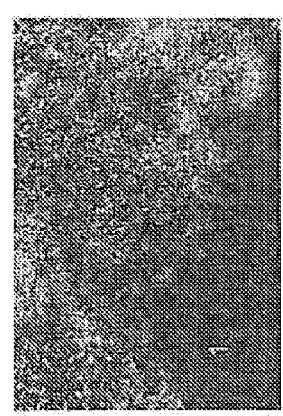
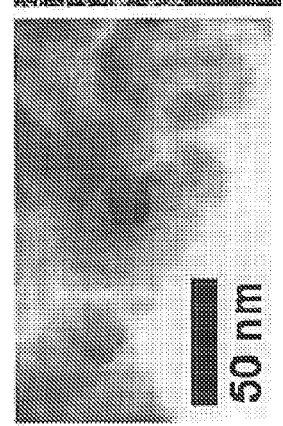
Figure 7 (g),(h),(i),(j)

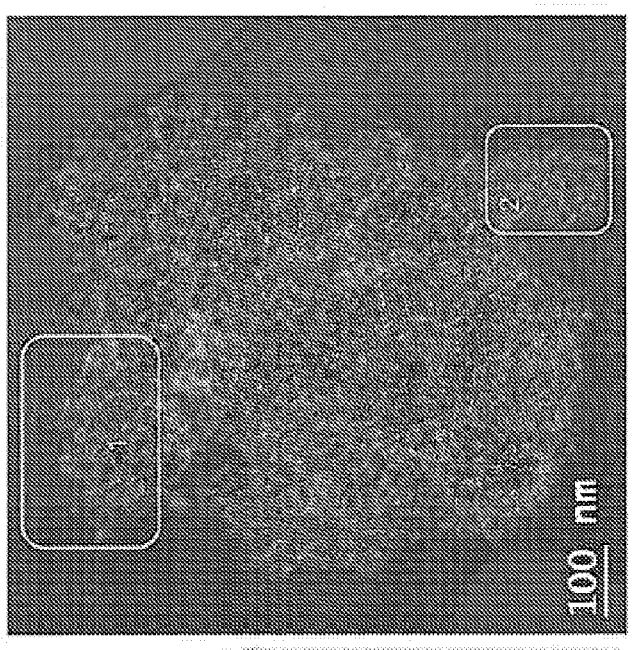
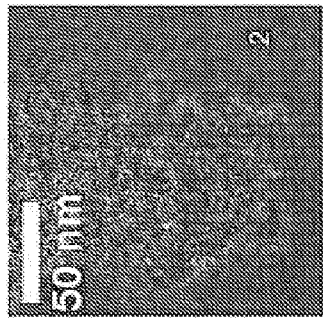
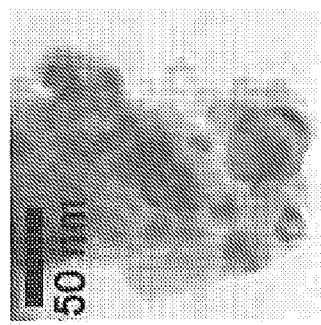
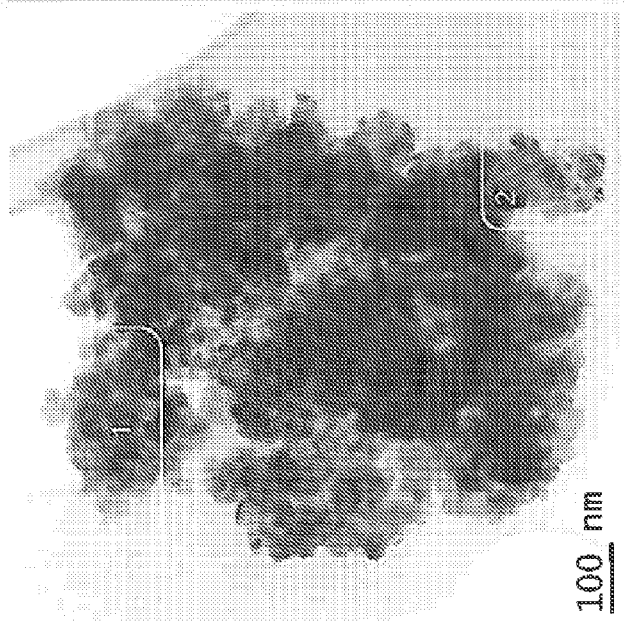
Figure 10 (a),(b)
Figure 10 (c),(d)
Figure 10 (e),(f)

Figure 11
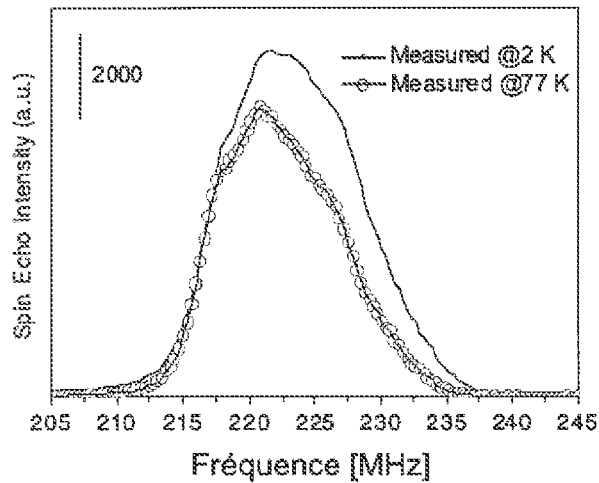
Figure 11 a
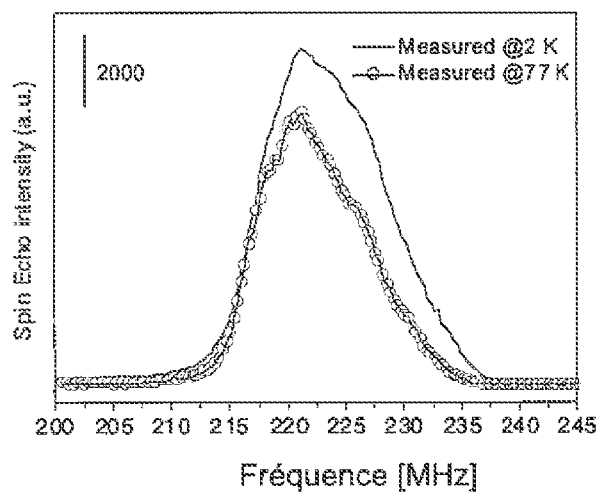
Figure 11 b
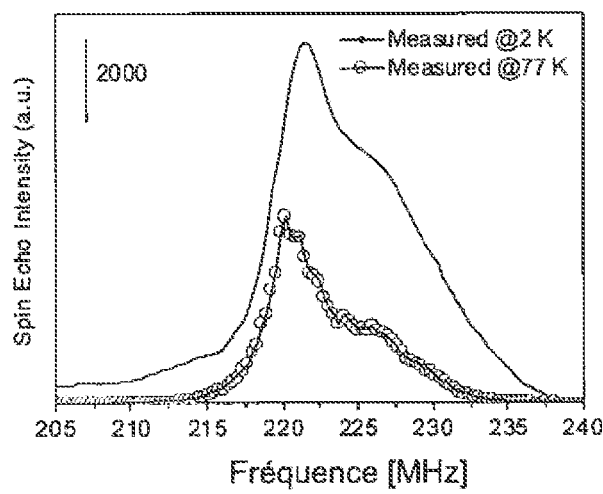
Figure 11 c

CATALYST SUPPORTS MADE FROM SILICON CARBIDE COVERED WITH TIO₂ FOR FISCHER-TROPSCH SYNTHESIS

CROSS-REFERENCE TO RELATED APPLICATIONS

The present application is a National Stage Application of PCT International Application No. PCT/FR2013/051465 (filed on Jun. 24, 2013), under 35 U.S.C. §371, which claims priority to French Patent Application Nos. 1256028 (filed on Jun. 26, 2012) and 1257446 (filed on Jul. 31, 2012), which are each hereby incorporated by reference in their respective entireties.

TECHNICAL FIELD

The invention relates to heterogeneous catalysis, and more specifically catalysts supports and catalysts capable of being used in heterogeneous catalysis. It relates in particular to a novel catalyst support and a novel catalyst for the Fischer-Tropsch reaction. This novel catalyst support belongs to the porous supports based on silicon carbide (SiC), in particular based on β-SiC, modified by a surface deposit of $TiO_2$.

BACKGROUND

The Fischer-Tropsch reaction converts a mixture of CO and hydrogen into hydrocarbons. There are two types of catalyst for the Fischer-Tropsch reaction: iron-based catalysts, which work optimally at a temperature on the order of 350° C. (called "high-temperature FT catalyst"), and cobalt-based catalysts, which work at a lower temperature, generally below 250° C. They are primarily comprised of an active phase and an oxide support. A summary of the prior art on catalysts for the FT reaction based on cobalt is provided in the article "On the selectivity of cobalt-based Fischer-Tropsch catalysts: Evidence for a common precursor for methane and long-chain hydrocarbons" by S. Lögdberg et al., published in 2010 in J. Catalysis (doi:10.1016/jcat.2010.06.007). The oxide supports consist primarily of alumina, silica and optionally titanium dioxide. The oxide supports have excellent properties making it possible to design active catalysts for the FT reaction, but they also suffer from disadvantages such as their very low thermal conductivity, low hydrothermal resistance, the presence of acid sites at the surface (alumina), low mechanical strength in particular for extrudates (silica and titanium dioxide) and low attrition resistance for microbeads used in a bubbling bed (in particular for silica and $TiO_2$).

To increase the mechanical and hydrothermal stability of the oxide supports, it has been sought to modify these supports. Mention may be made of alumina promoted by lanthanum oxide $La_2O_3$ (U.S. Pat. No. 5,537,945 and U.S. Pat. No. 6,255,358 (Energy International Corp.), U.S. Pat. No. 7,163,963 (Conoco Phillips Co.)), by Si (U.S. Patent Publication No. 2005/0124490 (Chevron Texaco Corp.), U.S. Pat. No. 7,365,040 (Sasol Technology)) and by Ti or Zr (U.S. Pat. No. 6,975,7209 (Sasol Technology)). Spinel supports have also been proposed (patent applications WO 2006/067285 (Institut Français du Pétrole) and U.S. Patent Publication No. 2007/0161714), as well as amorphous silica supports (U.S. Patent Publication No. 2010/0311570) for increasing attrition resistance. The alumina used is generally predominantly alumina-γ, but alumina supports including a majority of alumina-α have also been used (U.S. Pat. No. 7,351,679 (Statoil ASA)).

It has been reported in the literature that $TiO_2$ supports make it possible to produce extremely selective cobalt-based catalysts ($C_{5+}$) for the FT (see the publications published in the journal Catalysis Today, vol. 100 (2005), p. 343-347 and in the Journal of Catalysis, vol. 236 (2005), p. 139, as well as in Applied Catalysis A: General, vol. 210 (2001) p. 137-150). However, the authors mention that their mechanical strength is too low.

$TiO_2$ is generally used to increase interactions with particles of the active phase. It has been reported in the literature that a silica support covered with a layer of $TiO_2$ would make it possible to increase the activity and selectivity of a silica support. The results obtained on this type of silica-based support promoted with $TiO_2$ (see the publication "Influence of Support Preparation Methods on Structure and Catalytic Activity of $CoTiO_2$—$SiO_2$ for Fischer-Tropsch Synthesis" of S. Mu et al., published in 2009 in the journal Catal. Lett. 133, p. 341-345, and the publication of S. Hinchiranan et al. published in 2008 in the journal Fuel Proc. Technol. 89, p. 455-459) demonstrate a substantial improvement in the catalytic activity in FT synthesis. The introduction of $TiO_2$ in the support also modifies the liquid hydrocarbon selectivity. Nevertheless, according to the deposition mode and the configuration of the FT test, fixed bed or bubbling bed, the influence is different, e.g. an improvement in the case of a FT test in fixed-bed mode and a slight drop in the case of a test in stirred-bed mode. In every case, the improvement in the catalytic activity in FT is attributed to a better dispersion of the cobalt particles with a smaller size in the presence of $TiO_2$.

Finally, in tubular fixed-bed reactors, the use of catalysts supported on β-SiC makes it possible to temper the thermal variations in the catalytic bed owing to the high thermal conductivity of the β-SiC material. All of these advantages make it possible to perform the FT synthesis under more extreme conditions in order to improve the productivity of the method.

Nevertheless, a catalyst supported on a β-SiC material is less active than its homologs supported on oxides.

The present invention is intended to prepare a novel type of silicon carbide-based (SiC) support for the Fischer-Tropsch synthesis (FTS) reaction that has better stability and better efficiency as well as better selectivity.

SUMMARY

According to the invention, the problem is solved by depositing the active phase on a very finely titanium oxide ($TiO_2$) layer, consisting of nanoparticles, which at least partially covers the macroporous and mesoporous surface of the SiC porous support. The silicon carbide is preferably β-SiC having at least macroporosity and mesoporosity. It may, for example, be pellets, beads or a foam of β-SiC. The $TiO_2$ is preferably anatase.

The inventors observed that when cobalt is deposited on a support according to the invention based on silicon carbide (and in particular on a β-SiC cellular foam) covered with TiO2, this makes it possible to significantly increase the activity in FT synthesis, while maintaining a relatively high liquid hydrocarbon selectivity above 90%. The method for deposition of the superficial TiO2 layer is easy to implement, for all types and forms of support.

This mixed support has beneficial properties resulting both from the beta polytype of the silicon carbide (β-SiC) and the titanium dioxide, in particular in its anatase form. Among these properties, mention may be made, with regard to β-SiC, of its excellent thermal conductivity, a meso- and macroporous bimodal porosity, an excellent chemical and hydrothermal resistance as well as good mechanical strength. The titanium dioxide in its anatase form enables the fine dispersion of active-phase particles.

The synthesis method according to the invention makes it possible to control, as desired, the morphology and size of the supports according to the configuration of the reactors used. The catalysts prepared from these TiO2-covered supports have a high FTS activity by comparison with that measured on a homolog catalyst deposited on β-SiC without a TiO2 layer. In addition, the catalytic performances of these catalysts supported on TiO2-covered β-SiC are very stable over time.

According to an essential aspect of the invention, the TiO2 deposition is performed by a sol-gel method involving a liquid phase of a TiO2 precursor. This gives better results by comparison with a crystal TiO2 deposit, for example from a dispersion of TiO2 powder (known method leading to a "wash-coat" deposit). More specifically, this method involves the following steps: (a) a highly porous β-SiC support is provided, (b) a solution of at least one TiO2 precursor is prepared, (c) said support is impregnated by said solution, (d) said impregnated support is dried, (e) said impregnated support is calcined in order to transform said TiO2 precursor into TiO2.

This method leads to the formation of TiO2 crystallites on the mesoporous and macroporous surface. This prevents the formation of a crust on the macroporous surface that prevents access of reaction gases to the mesopores and micropores. This is reflected by the fact that the porous distribution of the support is not significantly modified by the TiO2 crystallite deposit on the mesoporous and macroporous surface of the support.

In this method, said β-SiC support may in particular be in the form of extrudates, pellets, beads, microbeads or cellular foam.

The specific surface of the support resulting from the method according to the invention is at least 15 m2/g, and preferably at least 20 m2/g.

The microporous contribution to the specific surface of said support is advantageously less than 5 m2/g, and even more preferably less than 3.5 m2/g.

Said calcination (step (e)) is preferably performed at a temperature of between 400° C. and 1000° C., and preferably between 500° C. and 900° C. The temperature increase is advantageously produced with a gradient of between 1.5° C./min and 3.5° C./min, and preferably between 1.5° C./min and 2.5° C./min.

The catalyst support capable of being obtained by the method described above advantageously has a mass content (in %) of TiO2 with respect to that of SiC (see the "Definitions" section below) of between 3% and 30%, preferably between 5% and 20%, even more preferably between 8% and 16% and optimally between 8% and 13%. Advantageously, its TiO2 content is less than 0.02 g per m2 of specific surface of the SiC support, and preferably less than 0.013 g per m2 of specific surface of the SiC support, and even more preferably less than 0.009 g per m2 of specific surface of the SiC support.

On the catalyst support capable of being obtained by the method described above, it is possible to deposit an active phase in order to obtain a catalyst. Said active phase is metallic cobalt, metallic iron or a mixture of the two, finely divided. Advantageously, the catalyst includes between 5% and 40% by mass, and preferably between 10% and 25% by mass (expressed with respect to the mass of the support) of cobalt on a support of which the TiO2/SiC mass ratio is between 5% and 20%, preferably between 8% and 16%, and even more preferably between 8% and 13%.

Thus, the first object of the invention is the use for the Fischer-Tropsch reaction of an SiC-based catalyst support at least partially covered with TiO2 capable of being obtained by the preparation method described above, or of a catalyst obtained by the deposition of an active phase on said catalyst support, said active phase being metallic cobalt, metallic iron or a mixture of the two, finely divided. The use according to claim 1, in which said β-SiC support is in the form of extrudates, pellets, beads, microbeads or cellular foam.

Advantageously, the specific surface of said support is at least 15 m2/g, and preferably at least 20 m2/g. The microporous contribution to the specific surface of said support is less than 5 m2/g. In the method for preparing the support, said calcination is performed at a temperature of between 400° C. and 1000° C., and preferably between 500° C. and 900° C. In the calcination step, the temperature increase is produced with a gradient of between 1.5° C./min and 3.5° C./min, and preferably between 1.5° C./min and 2.5° C./min.

A second object of the invention is a catalytic method for conversion of CO and hydrogen into hydrocarbons, characterized in that it involves a catalyst obtained by the deposition of an active phase on an SiC-based catalyst support at least partially covered with TiO2 capable of being obtained by the preparation method described above, said active phase being metallic cobalt, metallic iron or a mixture of the two, finely divided.

A third object of the invention is an SiC-based catalyst support at least partially covered with TiO2 capable of being obtained by a preparation method described above, which includes the following steps: (a) a highly porous β-SiC support is provided, (b) a solution of at least one TiO2 precursor is prepared, (c) said support is impregnated by said solution, (d) said impregnated support is dried, (e) said impregnated support is calcined in order to transform said TiO2 precursor into TiO2, or a catalyst obtained by the deposition of an active phase on said catalyst support, said active phase being metallic cobalt, metallic iron or a mixture of the two, finely divided, said catalyst support being characterized in that its TiO2 content is less than 0.02 g per m2 of specific surface of the SiC support, and preferably less than 0.013 g per m2 of specific surface of the SiC support, and even more preferably less than 0.009 g per m2 of specific surface of the SiC support.

In the catalyst according to the third object of the invention, the TiO2/SiC mass ratio is between 3% and 30%, preferably between 5% and 20%, even more preferably between 8% and 16%, and optimally between 8% and 13%. Its specific surface is advantageously at least 15 m2/g and preferably at least 20 m2/g. The microporous contribution to its specific surface is advantageously less than 5 m2/g. Said support may be in the form of extrudates, pellets, beads, microbeads or cellular foam.

DRAWINGS

FIGS. 1 to 11 show embodiments of the invention.

Figure 1C:
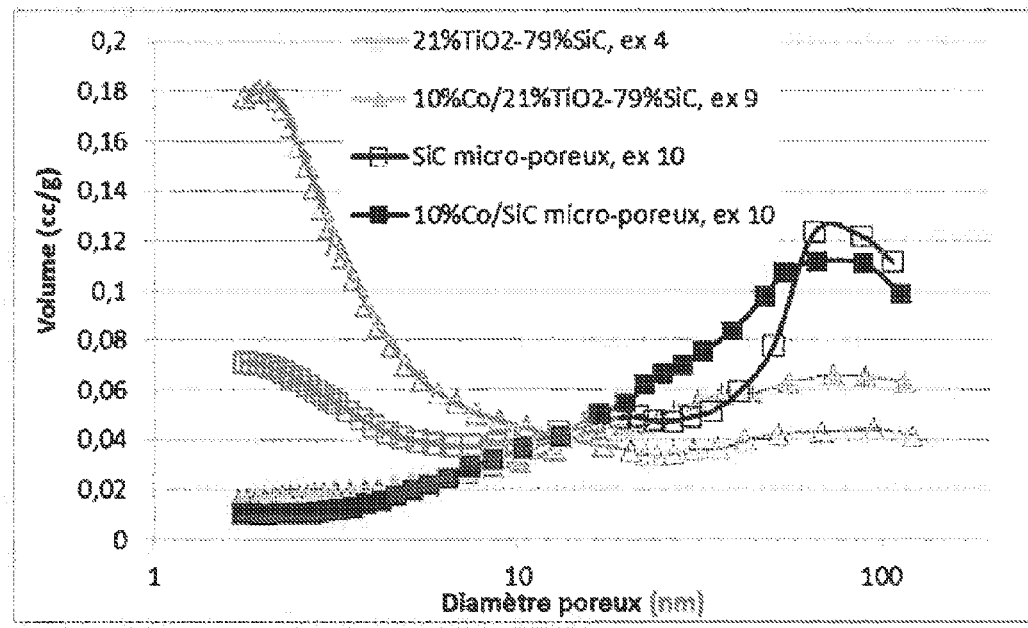

FIG. 1 shows pore distribution curves by nitrogen sorptometry. FIG. 1A shows these curves for three samples: β-SiC (diamonds); 10% TiO2/β-SiC according to example 2 (squares); 21% TiO2/79% β-SiC/according to example 4 (triangles). FIG. 1B shows, on the expanded x-axis, these curves for β-SiC (diamonds) et 10% TiO2/β-SiC according to example 2 (squares), these two samples being the same as in FIG. 1A, and in addition the corresponding curve for 10% Co/10% TiO2/β-SiC (cross) according to example 7. FIG. 1C shows these curves for four samples: microporous SiC according to example 10 (empty squares), microporous SiC with active phase of 10% Co according to example 10 (solid squares), 21% TiO2-79% β-SiC/according to example 4 (empty triangles), 10% Co/21% TiO2-79% SiC according to example 9.

Figure 2:
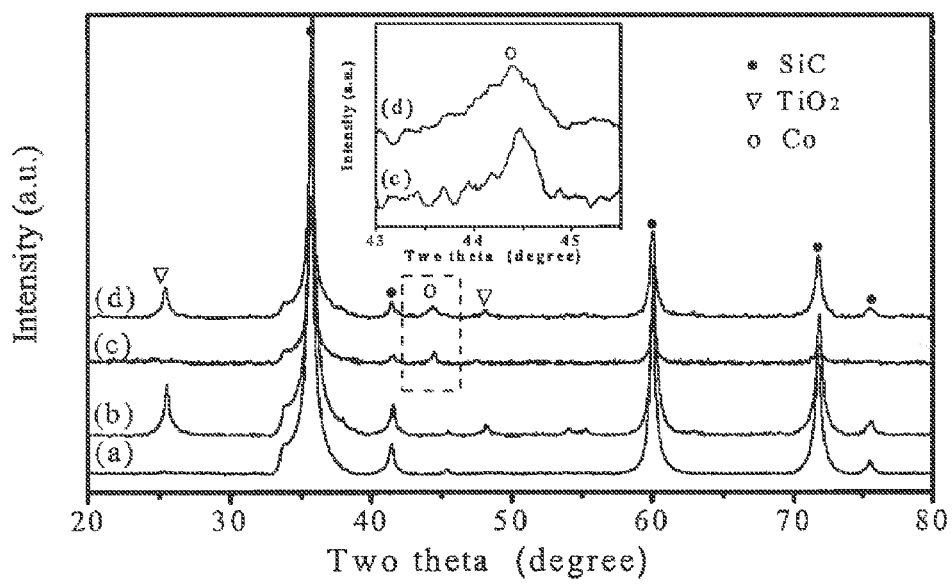

FIG. 2 shows the X-ray diffraction diagrams of the cobalt-based catalysts supported on β-SiC and 10% TiO2/β-SiC after calcination under air at 350° C. for 2 hours and reduction under H2 at 300° C. For comparison, the diagrams of the single support, pure and covered with TiO2, are also shown in the same figure. Insert: Enlargement on the diffraction peak of metallic cobalt demonstrating a broadening in the width at mid-height in the presence of TiO2. Samples: (a) β-SiC; (b) 10% TiO2/β-SiC (according to example 2); (c) 10% Co/β-SiC (according to example 5); (d) 10% Co/10% TiO2/β-SiC (according to example 7).

Figure 3:
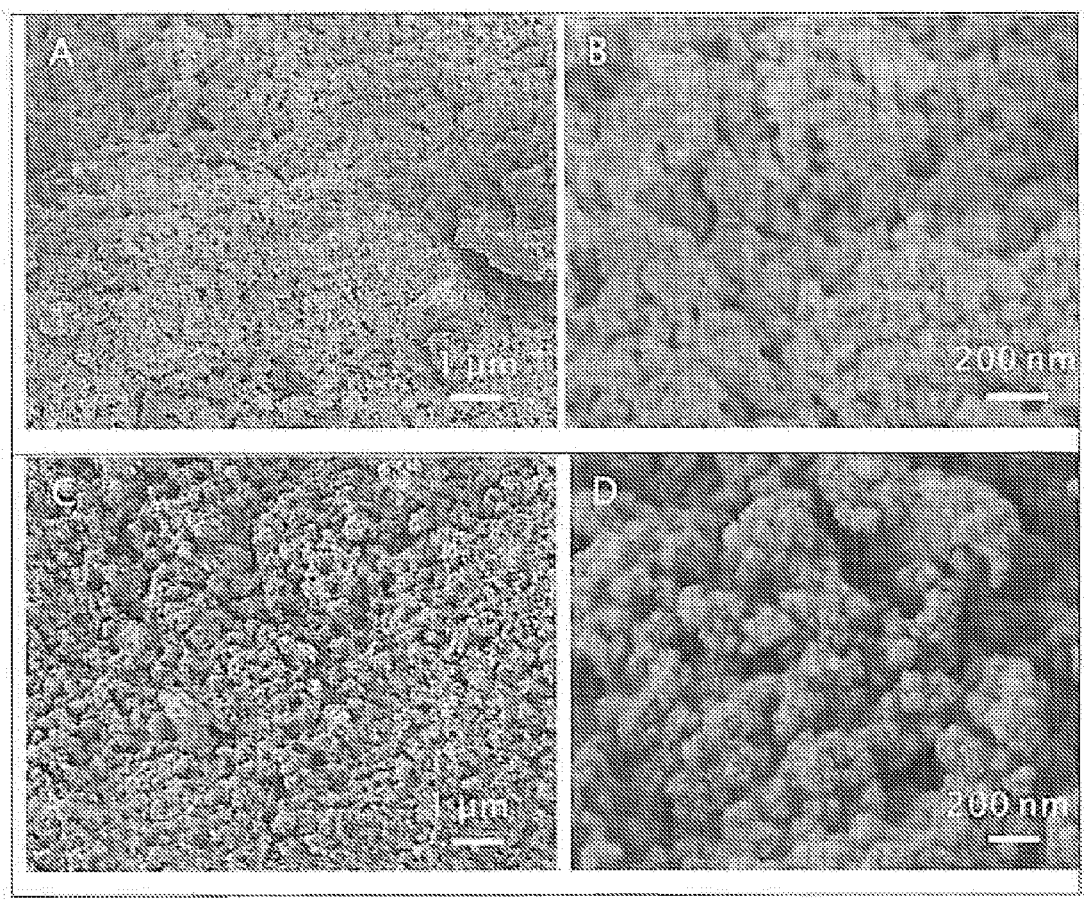

FIG. 3 shows micrographs obtained by scanning electron microscopy (SEM) at different enlargements of two samples: (A) and (B): 10% Co/β-SiC (according to example 5). (C) and (D): 10% Co/10% TiO2/β-SiC (according to example 7). The length of the bars is indicated at the lower right-hand side of each micrograph: 1 μm (A) and (C), 200 nm (B) and (D).

FIG. 4 shows a micrograph obtained by transmission electron microscopy (TEM) of an area of the 10% TiO2/β-SiC support obtained according to example 2. FIG. 4(a) shows the SEM image, FIG. 4(b) shows the chemical mapping obtained in energy-filtering mode making it possible to identify the areas containing Ti (in white) and those containing Si (dark). It is observed that the TiO2 clearly covers the SiC particles. The bar length corresponds to 50 nm.

FIG. 5 shows two views obtained by energy-filtered transmission electron microscopy (EFTEM) with transmission in energy filtering mode and in a three-dimensional representation of an area of the 10% Co/21% TiO2-79% β-SiC catalyst according to example 9 (comparative) in chemical mapping mode (the two images correspond to the front and back of the same area). The distribution of TiO2 (in white) and SiC (in gray) distributed at the surface of the solid can be seen. Two types of cobalt particles are observed (in black): large particles deposited on the SiC areas and several rare particles, clearly smaller, deposited on the TiO2 areas.

FIG. 6 shows two other micrographs obtained by transmission electron microscopy in a transverse cross-section of two particles (FIGS. 6(a) and (b)) of 10% Co/21% TiO2-79% β-SiC catalyst according to example 9 (comparative). The images were taken in electron energy loss spectroscopy mode (EELS). Colors: white=Co; black=Ti; gray=Si.

FIG. 7 relates to a 10% Co/10% TiO2/SiC catalyst according to the invention. It shows a micrograph obtained by transmission electron microscopy (TEM) (FIG. 7(a)) and in energy-filtering mode (EFTEM) (FIGS. 7(b), 7(c), 7(d) respectively for the mapping of Si, Ti and Co)) of an area of the 10% Co/10% TiO2/β-SiC catalyst according to example 7. FIG. 7(d) makes it possible to estimate an average size of the cobalt particles at around 20 nm, the bar length being 100 nm. FIGS. 7(e) and 7(f) show the same images as FIGS. 7(a) and 7(c); they are slightly enlarged. The areas marked (1) and (2) in FIGS. 7(e) and 7(f) are enlarged in FIGS. 7(g) and (h) for area (1) and in FIGS. 7(i) and (j) for area (2), with the understanding that FIGS. 7(g) and (i) are TEM micrographs and FIGS. 7(h) and (j) area EFTEM micrographs of titanium; the bar length is 50 nm.

Figure 8:
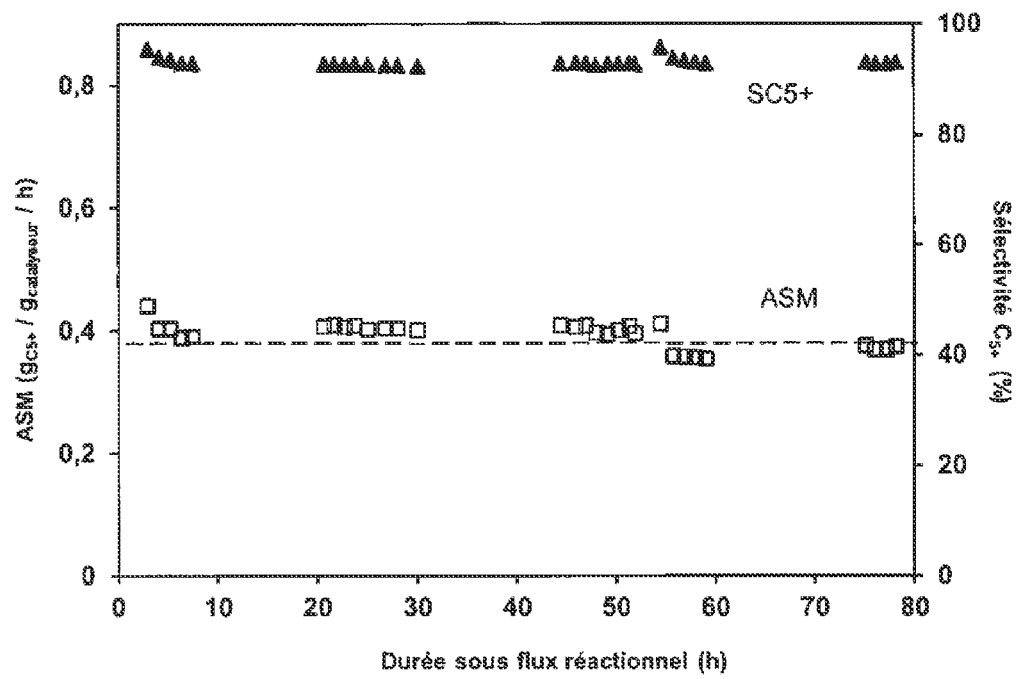

FIG. 8 shows the specific mass activity and the liquid hydrocarbon selectivity (SC5+) obtained with the 10% Co/10% TiO2/β-SiC catalyst according to example 7 as a function of the time of the test. The ratio H2/CO was 2, the reaction temperature was 215° C., the total pressure 40 atmospheres, and the gas hourly space velocity (GHSV) 2850 h−1.

Figure 9:
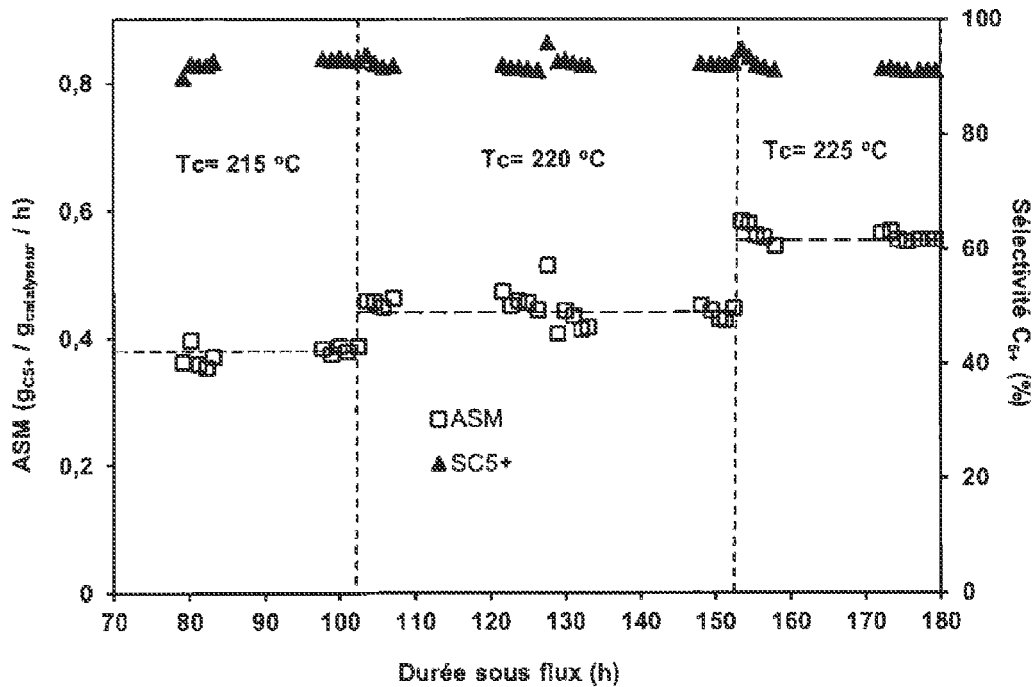

FIG. 9 shows the specific mass activity and the liquid hydrocarbon selectivity (SC5+) obtained on the 10% Co/10% TiO2/β-SiC catalyst according to example 7 as a function of the reaction temperature. The ratio H2/CO was 2, the total pressure 40 atmospheres, and the gas hourly space velocity (GHSV)=3800 h−1.

FIG. 10 shows a second area of the same sample as FIG. 7. FIGS. 10(a), (c) and (e) are TEM micrographs, FIGS. 10(b), (d) and (f) are EFTEM micrographs of titanium. FIGS. 10(c) and (d) correspond to area (1), and FIGS. 10(e) and (f) to area (2).

FIG. 11 shows spectra obtained by nuclear magnetic resonance of 59Co on cobalt-based catalysts deposited on different supports: 10% Co/SiC according to example n° 5 (comparative)(FIG. 11a), 10% Co/21% TiO2-79% SiC according to example n° 9 (comparative)(FIG. 11b), 10% Co/10% TiO2/SiC according to example n° 7 (FIG. 11c). The intensity of the spin echo is represented in arbitrary units. The solid curves were recorded at a temperature of 2K, and the point curves were recorded at a temperature of 77K.

DESCRIPTION

Definitions

In the context of this invention, the term "specific surface" means the specific surface determined according to the method of Brunauer, Emmet and Teller (BET method), well known to a person skilled in the art and described in particular in standard NF X 11-621.

The porosity of a material is normally defined by reference to three categories of pores that are distinguished by their size: microporosity (diameter smaller than 2 nm), mesoporosity (diameter of between 2 nm and 50 nm) and macroporosity (diameter greater than around 50 nm).

In certain embodiments of this invention, a β-SiC foam is used, which is in the form of an open-pore cellular foam. By "cellular foam", we mean a foam that has both a very low density and a large porous volume. The size of the cell opening is variable and is typically between around 800 and 6000 μm. Such a foam can be prepared using known techniques. It has a very low microporosity. The mesoporosity is essentially associated with the bridges that form the cells. The open macroporosity of such a foam may vary from 30 to 95%, in particular 50 to 90%, and its volume density may be between 0.05 g/cm3 and 0.5 g/cm3. In general, for its use as a catalyst support or catalyst, below a density of 0.05 g/cm3, problems of mechanical stability of the foam are encountered, while above 0.5 g/cm3, the porous cell volume will be reduced and the head loses will increase without providing any functional advantage. Advantageously, the density is between 0.1 and 0.4 g/cm3.

In other embodiments of this invention, β-SiC is used in the form of extrudates, pellets, microbeads or grains. This material can be prepared by means of known techniques.

Mode of Synthesis of the Support

According to one embodiment, a highly porous β-SiC support is impregnated with an organic solution of a TiO2 precursor. Said TiO2 precursor can be an organic precursor, in particular an alcoholate. Ti(i-OC3H7)4 (abbreviated TTIP) is preferred. The solvent can be an alcohol, for example ethanol or i-propanol. Advantageously, an ethanol solution is used (preferably anhydrous in order to prevent hydrolysis of the TTIP) containing Ti(i-OC3H7)4 (distributed, for example by the Acros company).

In an advantageous embodiment, the molar ratio Ti/Si is between 2.5% and 10% (i.e. a TiO2 load of between 5% and 20% by mass with respect to the total mass of SiC). After impregnation, the solid is dried, for example in an oven at 110° C. for 8 hours. Advantageously, the solid is left after impregnation at room temperature (for example for 4 hours) before drying. The transformation of the precursor into $TiO_2$ is performed by calcination (advantageously under air), preferably at a temperature of between around 400° C. and around 1000° C.). The temperature increase gradient is advantageously between 1.5° C./min and 3.5° C./min, and preferably around 2° C./min. As an example, the calcination temperature can be 600° C. and the treatment time at this temperature can be 5 hours.

By way of comparison, it is also possible to prepare a hybrid material containing similar $TiO_2$ and SiC contents, but in which the two phases are distributed in the entire solid mass, by contrast with the materials preferred here, in which an SiC core is covered with a $TiO_2$ layer; such a hybrid support is not covered by this invention.

To avoid any confusion in the notations, "x % $TiO_2$/SiC" will refer to solids formed by a superficial layer of $TiO_2$ (or at least by individual $TiO_2$ particles) deposited on an SiC support in the amount of a content at x % with respect to the mass of SiC, and "y % $TiO_2$-SiC" will refer to mixed solids (also called "hybrids") containing y % $TiO_2$ and (100−y) % SiC distributed in the mass of the material, with the understanding that x and y express mass percentages.

The method according to the invention ensures a good dispersion of the fine $TiO_2$ particles over the entire macroporous and mesoporous surface, outer and inner, of the support. It prevents the formation of thick layers or crusts. The deposition of $TiO_2$ crystallites from a liquid dispersion according to the prior art (forming a layer that a person skilled in the art calls a "wash coat") does not make it possible to obtain such a fine dispersion in the depth of the β-SiC support.

The β-SiC support may have any suitable geometric shape. It may in particular involve extruded pellets. It may also involve β-SiC foam. These supports are known as such and can be prepared by one of the known methods, namely: (i) impregnation of a polyurethane foam with a suspension of a silicon powder in an organic resin (Prin process, see EP 0 624 560 B1, EP 0 836 882 B1 and EP 1 007 207 A1); (ii) the reaction between SiO vapors and reactive carbon at a temperature of between 1100° C. and 1400° C. (Ledoux process, see EP 0 313 480 B1); or (iii) cross-linking, carbonization and carburation of a mixture of a liquid or pasty prepolymer and a silicon powder (Dubots process, see EP 0 440 569 B1 and EP 0 952 889 B1).

Mode of Preparation of the Catalyst on the Support

On the $TiO_2$/SiC support according to the invention, an active phase consisting of one or more transition metals is deposited. Iron, cobalt or a mixture of the two is preferred. This deposition is advantageously performed by the method of impregnation of the porous volume with a solution of a precursor of the active phase, which is known to a person skilled in the art. Said precursor can be a solution of at least one organometallic compound of the metal which will constitute the active phase, or an organic salt thereof. After impregnation, the solid is dried (preferably at a temperature of between 100° C. and 140° C.) then calcined (preferably under air at a temperature of between 250° C. and 450°, and preferably with a heating gradient of between 0.6° C./min and 1.6° C./min) to obtain an oxide of said metal. The active phase is obtained by reduction of the oxide precursor, preferably at a temperature of between 200° C. and 380° C. (and preferably with a heating gradient of between 2° C./min and 4° C./min).

The average size (d) of the active phase particles (i.e. their average diameter) is advantageously between 15 nm and 40 nm. It may be estimated either on the basis of the size of the oxide precursor, which is chemically stable and therefore easier to manipulate with a view to its characterization (for iron and cobalt, the particle size is approximately 0.75 times that of the oxide particles), or on the basis of the broadening of the diffraction peak according to the Scherrer formula, which is well known: $d=k\lambda/(\tau \cdot \cos\theta)$, where $\lambda$ represents the wavelength of the incident radiation, $\tau$ represents the width at mid-height of the diffraction peak, k is a constant and $\theta$ is one-half of the deviation of the wave.

In an advantageous embodiment of this step, after impregnation, the solid is dried in ambient air for 4 hours, then in an oven at 110° C. for 8 hours. The solid thus dried is calcined under air at 350° C. (gradient of 1° C./min) for 2 hours in order to obtain the oxide precursor of the catalyst, $Co_3O_4$/$xTiO_2$/SiC. The catalyst is obtained by reduction of the oxide precursor under a hydrogen flow at 300° C. (gradient of 3° C./min) for 6 hours. The catalyst is then denoted yCo/$xTiO_2$/SiC with y representing the load (in percent) of cobalt on the catalyst ([Co]/[$TiO_2$+SiC]) and x representing the load (in percent) of $TiO_2$ on the SiC support ([$TiO_2$]/[SiC]). The average size of the Co particles is around 20 nm.

Use of the Catalyst

The catalyst according to the invention is specifically designed for the Fischer-Tropsch reaction, and more generally for the catalytic conversion of a mixture of CO and hydrogen into hydrocarbons. The support may have any suitable geometric shape, and may be in the form of pellets, beads, microbeads, extrudates or in the form of foam plates or cylinders.

The best results are obtained with a catalyst, the support of which has a $TiO_2$/SiC mass ratio of between 8% and 16%, and optimally between 8% and 13%.

Advantages

The additional advantages in the use of such a catalytic system with respect to those currently reported in the literature are the following: (i) easy shaping of the support according to the nature of the reactor used, (ii) perfect control of the meso- and macroporous distribution of the support enabling better accessibility of the reactants and better removal of the intermediate reaction products, (iii) higher thermal conductivity of the support, with respect to silica or alumina, making it possible to reduce the formation of hot spots on the surface of the catalyst, with the understanding that hot spots may lead to degradation of the selectivity and also promote sintering of the active phase particles, (iv) higher mechanical stability with respect to the macroscopic $TiO_2$ supports (extrudates, foam, rings, beads, etc.) and better attrition resistance, because the $TiO_2$ is in the porosity of the support and not on its surface. This attrition resistance is a particularly important property if the catalyst is used in the form of microbeads in a "slurry"-type reactor.

EXAMPLES

Examples No. 1 to 3 (According to the Invention)

Deposition of $TiO_2$ on SiC Support

Porous SiC grains having a specific surface of 40 m2/g and a pore distribution free of micropores were provided. The porous volume of the grains was impregnated with an ethanol solution containing Ti(i-$OC_3H_7$)4 in an amount necessary for depositing a Ti load corresponding to 5% $TiO_2$, 10% $TiO_2$ and 15% TiO2 with respect to the SiC weight, respectively for the materials of examples no. 1, 2 and 3.

After impregnation, the solids were left at room temperature for 4 hours, then dried in the oven at 110° C. for 8 hours. The transformation of the precursor salt into TiO2 was then performed by calcination under air at 600° C. for 5 hours with a temperature increase gradient of 2° C./min. The materials thus obtained have specific surfaces, respectively, of 38 m2/g, 41 m2/g and 41 m2/g for examples 1, 2 and 3. The pore distribution of the starting SiC and of the 10% TiO2/SiC support are reported in FIG. 1A.

FIG. 4(b) shows an EFTEM (Energy Filtered Transmission Electron Microscopy) image obtained on the 10% TiO2/SiC support. The left-hand image n° 4(a) is a TEM cross-section image making it possible to see the entire sample. The image of FIG. 4(b) clearly shows the presence of a fine layer of TiO2 covering the porous surface of the SiC grain.

Example No. 4 (Comparative)

Preparation of a Mixed TiO2-SiC Support Containing 21% TiO2 and 79% SiC

A mixed TiO2-SiC material was prepared as follows:

1620 g of silicon powder, 1520 g of Novolac solid phenolic resin, 600 g of TiO2 powder (P25 of Degussa-Evonik, BET surface around 50 m2/g, average particle size on the order of 20 nm), 78 g of hexamethylenetetramine (HMT), 30 g Zusoplast powder plasticizer PS1, 200 g of a 35% polyvinyl alcohol solution and 1195 g of water were provided.

The powders were mixed. The polyvinyl alcohol was diluted in the quantity of water. An extrudable mixture was prepared by introducing, under stirring, the liquid mixture on the powders. Said mixture was extruded so as to form pellets with a diameter of 3 mm. After drying in ambient air, then at 150° C. for 4 h, the pellets were treated at 1360° C. under an argon flow for one hour. The solid obtained comprises 83.7% by mass of SiC and 16.3% by mass of TiC (i.e. a molar fraction of 11.5% Ti with respect to the sum of Ti+Si).

The X-ray diffraction diagram showed that the solid obtained is a mixture of SiC and TiC ("SiC—TiC composite"). Its specific BET surface was 54 m2/g, with 27 m2/g of microporous surface.

Then, said SiC—TiC composite was oxidized under air at 400° C. for 8 h. A composite of 20.6% by mass of TiO2-79.4% by mass SiC (i.e. a molar fraction of 11.5% Ti with respect to the sum of Ti+Si) with a mechanical strength of 59 N/mm was then obtained. Its specific surface is 83 m2/g, with 53 m2/g of microporous surface. FIG. 5 shows that the surface of this material is constituted by juxtaposed areas of SiC and TiO2 in equivalent quantities.

This material therefore has a composition similar to that of example 2, but its porous properties on the one hand and its surface composition on the other hand make it a very different catalytic support.

Example 5 (Comparative)

Preparation of a 10% Co/SiC Catalyst

A catalyst with 10% cobalt not containing titanium was prepared from the raw SiC already used in examples 1 to 3.

An aqueous solution of cobalt nitrate was prepared, which was impregnated on the SiC by the porous volume method. The cobalt nitrate concentration is calculated so as to obtain the desired cobalt load in the final catalyst. The solid was then dried in ambient air for 4 hours, then in the oven at 110° C. for 8 h. It was then subjected to calcination under air at 350° C. (gradient of 1° C./min) for 2 hours in order to obtain the oxide precursor of the catalyst, Co3O4/SiC. The 10% Co catalyst was then obtained by reduction of the oxide precursor under a hydrogen flow at 300° C. (gradient of 3° C./min) for 6 hours. Its specific surface was 33 m2/g. The average size of the Co particles is estimated at 40-50 nm (see table 1).

Examples 6 to 8 (According to the Invention)

Preparation of 10% Co/TiO2/SiC Catalysts

Example 5 was reproduced by replacing the SiC support with the solids prepared according to examples 1 to 3. The catalysts according to examples 6, 7 and 8, all containing a load of 10% Co were then obtained. The specific surface and the average diameter of the Co particles measured on said catalysts are reported in table 1.

With respect to the specific surfaces of the initial supports, the 10% Co catalysts deposited on the supports covered with a layer of TiO2 do not show any substantial modification of the specific surface, even though it is reduced from 40 m2/g to 33 m2/g after deposition of Co on SiC.

The presence of the TiO2 significantly influences the average size of the cobalt particles. Indeed, it thus goes from around 40-50 nm on SiC to 20 nm when the support has previously been covered with a layer at 10% by weight TiO2.

The X-ray diffraction diagrams of the catalysts are presented in FIG. 2. The diffraction peaks of the TiO2 phases are clearly visible in the diffraction diagrams. The diffraction also indicates that the reduction is (relatively) complete because diffraction peaks corresponding to the cobalt oxide, CoO and/or Co3O4 phase are not seen. The enlargement of the cobalt diffraction peak (insert of FIG. 2) in the diagrams shows that there is an increase in the width at mid-height of this peak, indicating that the size of the cobalt particles involved in the coherent diffraction is smaller in the presence of TiO2.

The SEM images of the catalysts of examples 5 and 7 (10% Co/SiC and 10% Co/10% TiO2/SiC) are presented in FIG. 3 and show a significant decrease in the size of the cobalt particles in the presence of TiO2. These results are consistent with those obtained by X-ray diffraction presented above: the dispersion of the cobalt particles is therefore significantly improved by the presence of the superficial TiO2 layer.

The EFTEM (Energy Filtered Transmission Electron Microscopy) images obtained on the 10% Co/10% TiO2/SiC catalyst are presented in FIG. 7. FIGS. 7(c) and 7(d) show the dispersion of the cobalt particles on the TiO2 layer. It is observed in the map of FIG. 7(d) that the average cobalt particle size is relatively small (on the order of 20 nm) and homogeneous. This result is consistent with those obtained from the broadening of the cobalt diffraction peaks presented above (table 1). FIG. 10, which refers to another area of the same sample, corroborates these results and conclusions.

Example 9 (Comparative)

Preparation of a 10% Co/21% TiO2-SiC Catalyst

A 10% Co catalyst was prepared according to example 5 by replacing the SiC support with the 21% TiO2-SiC mixed solid prepared in example 4. FIGS. 5 and 6 show that the catalyst obtained has two active phase populations: very large Co particles located at the surface of the SiC areas and some very small Co particles deposited on TiO2 areas. The solid prepared in example 4 has a specific surface of 83 m2/g and a large fraction of pores having a diameter smaller than 10 nm. After deposition of 10% Co, the specific surface falls to 25 m2/g. FIG. 1C reports the pore distributions of this support, as well as that of the catalyst obtained after deposition of 10% Co. It is observed that the pores having a small diameter have disappeared after deposition of the active phase.

Example 10 (Comparative)

Preparation and Test of a 10% Co/SiC Catalyst

A catalyst including an active cobalt phase was prepared (deposited by the method described in example 5) on a microporous SiC support of around 58 m2/g, with 27 m2/g micropores. After the deposition of the active phase, the specific surface measured is no more than 24 m2/g. FIG. 1C reports the pore distributions of the starting SiC sample, as well as that of the catalyst after deposition of 10% Co. The pores having a small diameter present on the original support have disappeared after deposition of the active phase, and are therefore of no use in the catalytic reaction.

Example 11

Evaluation of the Catalytic Performances of the Different Catalysts According to the Invention or According to the Comparative Examples The performances of the catalysts prepared according to examples 5, 6, 7, 8 and 9 were evaluated in the Fischer-Tropsch reaction. The results are reported in table 2. A doubling of the catalytic activity is observed for the catalyst containing a continuous layer of 10% TiO2 on SiC with respect to the catalyst prepared on SiC alone. The catalytic tests indicate that the TiO2 concentration has a significant influence on the catalytic performances of the cobalt-based catalysts with a mass cobalt concentration of 10%.

The results at 215° C. show that the activity in the Fischer-Tropsch reaction (expressed in terms of CoTY) is optimal for the catalysts loaded with 10% by mass of cobalt with a mass TiO2 concentration of 10%, while it is half as high for the lower TiO2 loads (5% by mass) or higher TiO2 loads (15% by mass). However, it should be noted that this optimal concentration of doping agent might be different according to the real cobalt load. Indeed, the optimal value of the TiO2 load could be made to be different when the cobalt load is increased, for example from 10% to 30% by mass.

It should be noted that the C5+ selectivity is slightly lower on the catalyst with 10% by mass of TiO2 with respect to the two other catalysts. This may be due to a higher conversion in the case of the catalyst loaded with 10% TiO2. The reduction in selectivity may be due to a smaller cobalt particle size, which has a tendency to produce light hydrocarbon products in the Fischer-Tropsch reaction.

We will now discuss in greater detail the performances of the catalysts prepared according to example 7. The stability of the catalytic performances of these catalysts (10% Co/10% TiO2/SiC) was evaluated and the results are presented in FIG. 8. It is clearly observed in this figure that the liquid hydrocarbon activity and selectivity of the catalyst are extremely stable as a function of the test time.

The influence of the reaction temperature on the activity of the catalyst of example 7 (10% Co/10% TiO2/SiC) in the Fischer-Tropsch test was also evaluated and the results are presented in FIG. 9 as well as in table 2. This table also presents other catalytic test results obtained with catalysts prepared according to other examples. It should be noted that in tests with the catalyst according to example 7, the gas hourly space velocity was increased from 2850 h−1 to 3800 h−1, in order to avoid excessive conversions that might lead to problems of thermal runaway in the catalytic bed. This thermal runaway may modify the characteristics of the active phase by sintering of the particles of the active phase. The FTS activity significantly increases the reaction temperature, while the liquid hydrocarbon selectivity remains high and stable. The specific mass activity reaches around 0.6 gc5+/gcatalyst/h with a liquid hydrocarbon selectivity of around 90% at 225° C. It should also be noted that the catalyst has a relatively high stability and no deactivation has been observed at each test stage.

By way of comparison, the catalyst prepared according to example 9 by depositing Co onto a mixed 21% TiO2-SiC material has a specific activity that is much lower than that measured on the catalysts of the invention.

These results demonstrate that the catalysts prepared according to the invention have very good catalytic performances for the FT reaction, and excellent stability over time.

Example 12

Characterization of Catalysts by NMR

The example below concerns the influence of the nature of the support on the dispersion of the cobalt particles. For example, three SiC-based catalysts were tested: on pure SiC (noted 10% Co/SiC according to comparative example no. 5), on SiC doped with 21% TiO2 (noted 10% Co/21% TiO2-79% SiC, according to comparative example no. 9) and on SiC covered with a layer of TiO2 deposited post-synthesis (noted 10% Co/10% TiO2/SiC, according to example no. 7). The analysis of the dispersion of cobalt particles on the different catalysts is performed by NMR of the 59Co (P. Panissod, C. Meny, Appl. Magn. Reson. 19, 447, 2000).

The NMR analysis of the 59Co indicates that the number of cobalt particles having a size smaller than 8 nm was significantly increased on the 10% Co/10% TiO2/SiC catalyst with respect to those of the two other catalysts. Indeed, the number of cobalt atoms forming particles having a size <8 nm, determined by the difference between the curve obtained at two blocking temperatures: 2 K and that at 77 K (see figure no. 11), is around 70% on the 10% Co/10% TiO2/SiC catalyst while it is only 33% for the 10% Co/21% TiO2-79% SiC catalyst and 28% for the 10% Co/SiC catalyst. The results thus obtained confirm that the deposition of a TiO2 layer on the surface of the SiC support made it possible to substantially improve the dispersion of the cobalt particles, which explains the significant improvement in the catalytic activity for the Fischer-Tropsch synthesis. It should be noted, however, that the size distribution obtained by NMR could be modified slightly from one catalyst to another and also that it does not take into account the formation of aggregates. Indeed, the formation of aggregates observed by transmission electron microscopy could lead to an underestimation of the average size of the cobalt particles in the catalyst.

TABLE 1

Characteristics of the supports and catalysts used for the FT synthesis

| Support | Specific surface [m2/g] | Co particle size (d(Co)) (a) [nm] | Co particle size (d(Co)) (b) [nm] |
|---|---|---|---|
| SiC | 40 | — | — |
| 5% TiO2/SiC (example 1) | 38 | — | — |

TABLE 1-continued

Characteristics of the supports and catalysts used for the FT synthesis

| | Specific surface [m2/g] | Co particle size (d(Co)) (a) [nm] | Co particle size (d(Co)) (b) [nm] |
|---|---|---|---|
| 10% TiO2/SiC (example 2) | 41 | — | — |
| 15% TiO2/SiC (example 3) | 41 | — | — |
| 21% TiO2/SiC2-79% SiC (example 4) (*) | 83 | — | — |
| Catalyst | | | |
| 10% Co/SiC (example 5) (*) | 32.7 | 42 ± 5 | 51 ± 5 |
| 10% Co/5% TiO2/SiC (example 6) | 36.7 | 31 ± 5 | 30 ± 5 |
| 10% Co/10% TiO2/SiC (example 7) | 40.4 | 24 ± 5 | 24 ± 5 |
| 10% Co/15% TiO2/SiC (example 8) | 40.7 | 34 ± 5 | NM |
| 10% Co/21% TiO2-79% SiC (example 9) (*) | 25.0 | NM | NM |
| (a) $d(Co) = 0.75 \times d(Co_3O_4)$ | (b) $d(Co) = k\lambda/(\tau \cdot \cos)$ determined on the basis of the diffraction plane (111) f.c.c. cobalt particles | (*) comparative example | |

TABLE 2

Catalytic performances in FT synthesis on the cobalt-based catalysts supported on SiC and SiC promoted with TiO2.
Reaction conditions: ratio H2/CO = 2, total pressure = 40 atmospheres

| Catalyst sample | T [° C.] | GHSV [h−1] | CO Conversion [%] | Selectivity [%] | | | Co TY (a) [h−1] | SMA (b) |
|---|---|---|---|---|---|---|---|---|
| | | | | CH4 | CO2 | C2-C4 | C5+ | |
| 10Co/SiC according to example no. 5 (comparative) | 215 | 2850 | 26.9 | 2.9 | 0 | 1.6 | 95.5 | 4.0 | 0.19 |
| | 220 | 2850 | 28.8 | 3.7 | 0 | 2.0 | 94.3 | 4.3 | 0.21 |
| | 225 | 2850 | 32.3 | 4.5 | 0 | 2.4 | 93.1 | 4.8 | 0.23 |
| | 230 | 2850 | 35.4 | 5.4 | 0.1 | 2.9 | 91.6 | 5.3 | 0.24 |
| 10Co/5TiO2/SiC according to example no. 6 | 215 | 2850 | 33.8 | 3.4 | 0 | 1.6 | 95.0 | 4.9 | 0.23 |
| | 220 | 2850 | 38.4 | 4.0 | 0 | 1.8 | 94.2 | 5.7 | 0.27 |
| | 225 | 2850 | 45.0 | 4.9 | 0 | 2.2 | 92.9 | 6.7 | 0.31 |
| | 230 | 2850 | 54.7 | 5.8 | 0.1 | 2.8 | 91.3 | 8.1 | 0.37 |
| 10Co/10TiO2/SiC according to example no. 7 | 215 | 2850 | 55.3 | 4.4 | 0 | 2.7 | 92.9 | 8.2 | 0.39 |
| | 215 | 3800 | 40.9 | 4.5 | 0 | 2.5 | 93.0 | 8.1 | 0.38 |
| | 220 | 3800 | 48.7 | 5.3 | 0 | 2.8 | 91.9 | 9.7 | 0.45 |
| | 225 | 3800 | 61.0 | 5.8 | 0.1 | 2.9 | 91.2 | 12.1 | 0.56 |
| 10Co/15TiO2/SiC according to example no. 8 | 215 | 2850 | 34.8 | 2.8 | 0 | 1.2 | 96.0 | 5.2 | 0.25 |
| | 220 | 2850 | 39.2 | 3.6 | 0 | 1.5 | 94.9 | 5.8 | 0.28 |
| | 225 | 2850 | 44.6 | 4.3 | 0 | 1.6 | 94.0 | 6.6 | 0.31 |
| | 230 | 2850 | 54.2 | 4.7 | 0 | 1.6 | 93.6 | 8.1 | 0.38 |
| 10Co/21TiO2/SiC according to example no. 9 (comparative) | 215 | 2750 | 36 | NM | NM | NM | 93 | NM | 0.17 |

(a) Co-Time Yield (CoTY): The yield per cobalt site represents the number of moles of CO converted per mass unit of cobalt per hour (i.e.: CO [mol]/Co[g]/[h]).

(b) Specific mass activity (SMA): The specific mass activity (SMSA) represents the mass of hydrocarbon (>C5) formed per gram of catalyst per hour (gc5+/gcatalyst/[h]).

NM means "not measured."

What is claimed is:

1. A method for catalytic conversion of CO and hydrogen into hydrocarbons, the method comprising: a catalyst having an active phase deposited on an SiC-based catalyst support, which is at least partially covered with $TiO_2$, the method further comprising:

providing a highly porous beta-SiC support;

preparing a solution of at least one $TiO_2$ precursor;

impregnating said highly porous beta-SiC by said solution;

drying and impregnated highly porous beta-SiC support; and calcining said impregnated highly porous beta-SiC support in order to transform said $TiO_2$ precursor into $TiO_2$.

2. The method of claim 1, wherein said catalyst includes between 10% and 25% by mass (expressed with respect to a mass of the support) of cobalt on a support of which the $TiO_2$/SiC mass ratio is between 8% and 13%.

3. The method of claim 1, wherein said β-sic support is in the form of extrudates, pellets, beads, microbeads or cellular foam.

4. The method of claim 1, wherein a specific surface of said support is at least 20 m$^2$/g.

5. The method of claim 4, wherein a microporous contribution to the specific surface of said support is less than 5 m$^2$/g.

6. The method of claim 1, wherein said calcination is performed at a temperature of between 500° C. and 900° C.

7. The method of claim 6, wherein, in the calcination, a temperature increase is produced with a gradient of between 1.5° C./min and 2.5° C./min.

8. The method of claim 1, wherein, in said catalyst support, a $TiO_2$/SiC mass ratio is between 8% and 13%.

9. The method of claim 1, wherein, in said catalyst support, a TiO$_2$ content is less than 0.009 g per m$^2$ of specific surface of the SiC support.

* * * * *